US00PP17075P2

(12) United States Plant Patent
Monet

(10) Patent No.: US PP17,075 P2
(45) Date of Patent: Sep. 5, 2006

(54) NECTARINE TREE 'MESEMBRINE'

(50) Latin Name: *Prunus persica*
Varietal Denomination: Mesembrine

(75) Inventor: Réné François Monet, Villenave D'Ornon (FR)

(73) Assignee: Agri-Obtentions, SA, Guyancourt Cedex (FR)

( * ) Notice: Subject to any disclaimer, the term of this patent is extended or adjusted under 35 U.S.C. 154(b) by 105 days.

(21) Appl. No.: 10/642,443

(22) Filed: Aug. 14, 2003

Related U.S. Application Data

(60) Provisional application No. 60/404,079, filed on Aug. 15, 2002.

(51) Int. Cl.
*A01H 5/00* (2006.01)

(52) U.S. Cl. ..... Plt./187

(58) Field of Classification Search ..... Plt./187, Plt./188, 190, 191
See application file for complete search history.

(56) References Cited

U.S. PATENT DOCUMENTS

PP12,438 P2 * 3/2002 Zaiger et al. ..... Plt./190

* cited by examiner

*Primary Examiner*—Anne Marie Grunberg
*Assistant Examiner*—Georgia Helmer
(74) *Attorney, Agent, or Firm*—Stratton Ballew PLLC

(57) ABSTRACT

A new cultivar of nectarine tree (*Prunus persica* L. Batsch) named 'Mesembrine' is disclosed. The fruit of 'Mesembrine' is notable for its broad oblate shape and sub-acid flavor.

4 Drawing Sheets

Latin name of the genus and species of the plant claimed: *Prunus persica* L. Batsch.
Variety denomination: 'Mesembrine'.

BRIEF DESCRIPTION OF THE PHOTOGRAPHS

Figure 1:
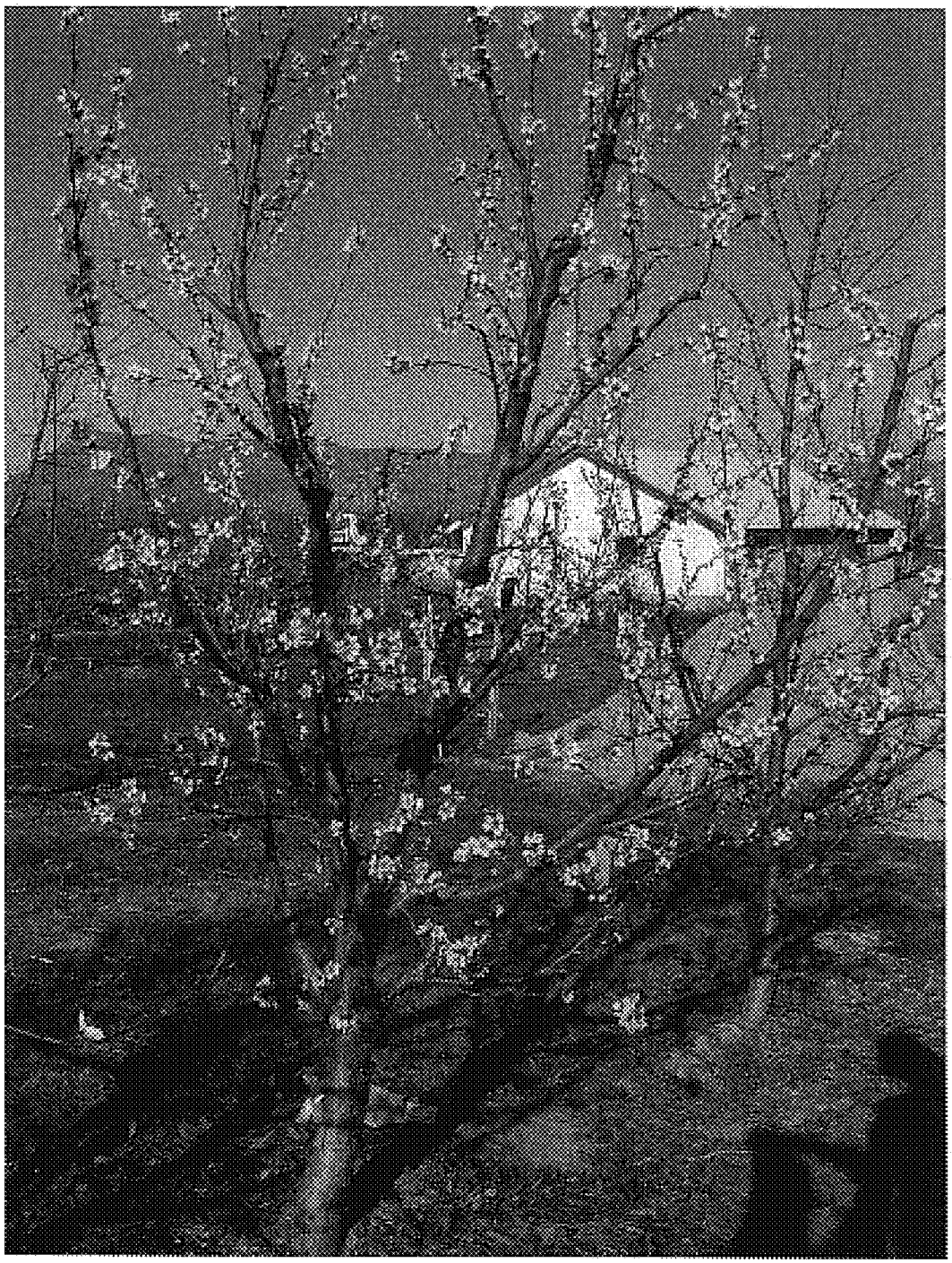
Figure 2:
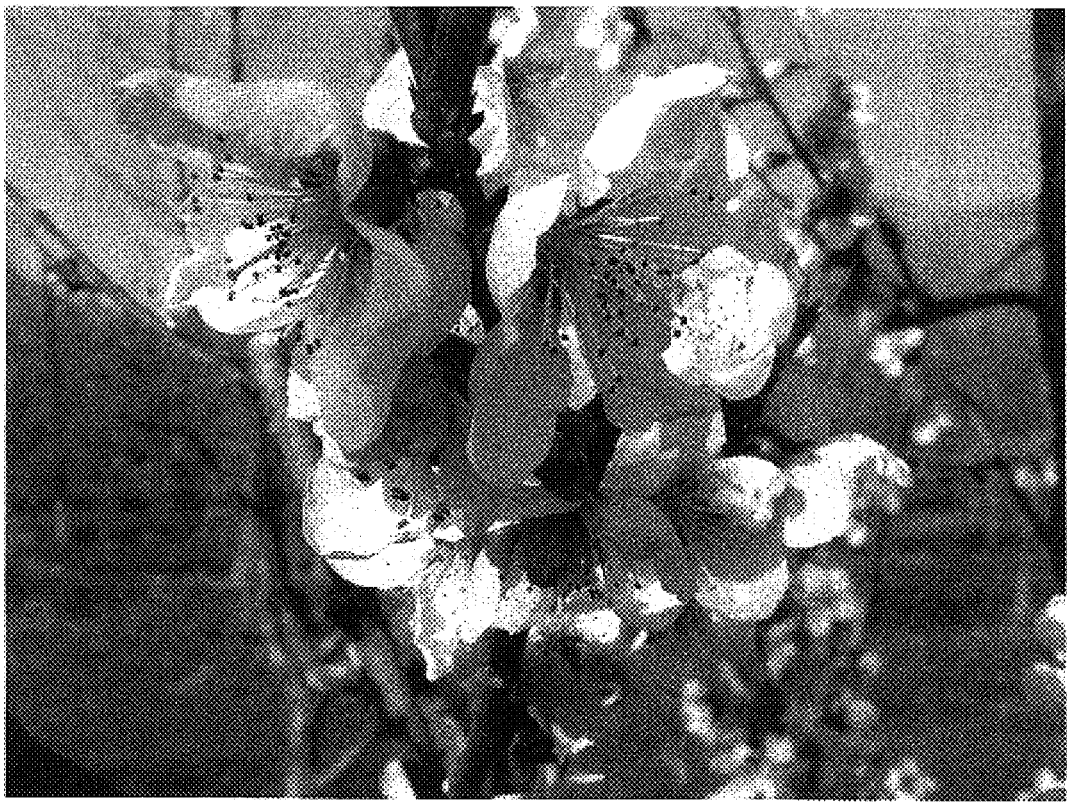
Figure 3:
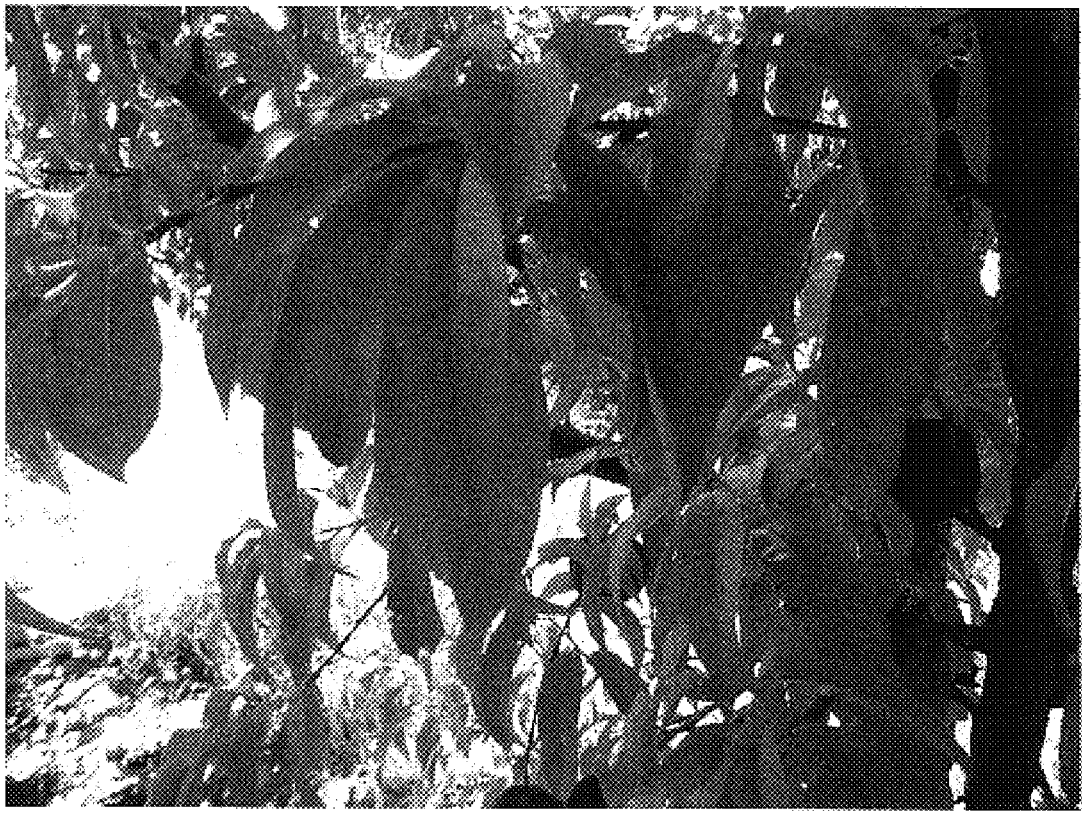
Figure 4:
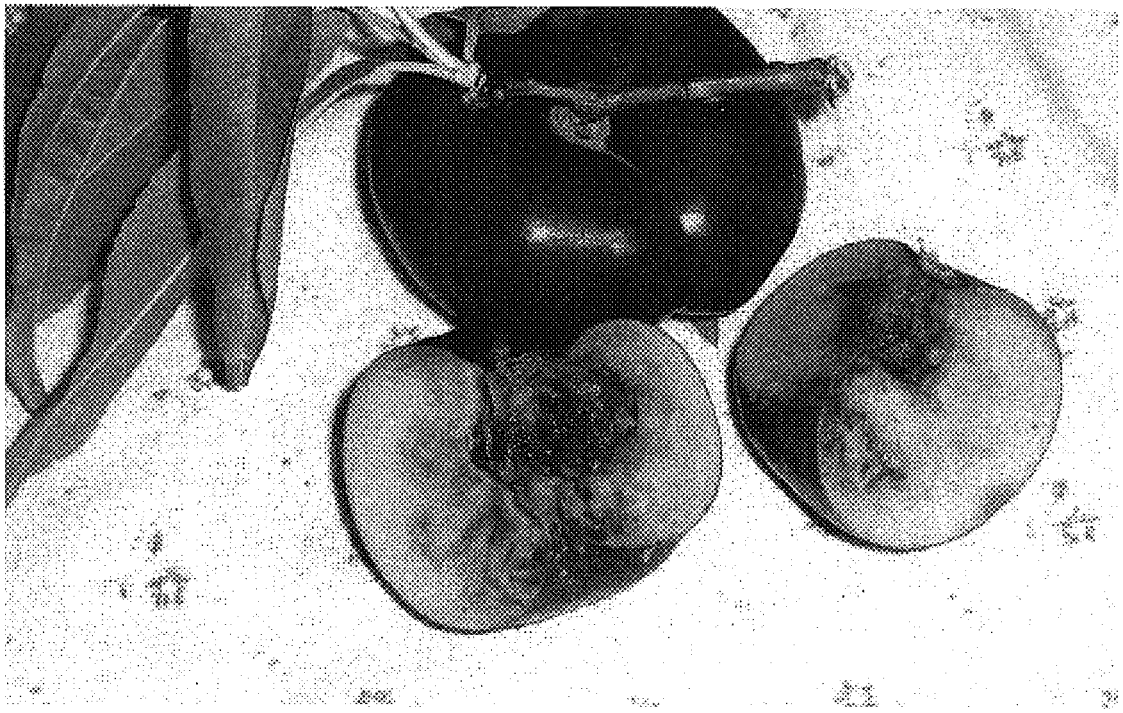

FIG. 1 shows the tree and blossoms of 'Mesembrine';
FIG. 2 shows the blossoms of 'Mesembrine';
FIG. 3 shows the leaves of 'Mesembrine'; and
FIG. 4 shows the fruit of 'Mesembrine'.

BRIEF DESCRIPTION OF THE VARIETY

The new nectarine tree 'Mesembrine' originated as a seedling resulting from a controlled cross of 'Jalousia'× 'Summergrand' (seed parent, not patented) and 'Fantasia' (pollen parent, not patented). Originally bred and tested by the Institut National de la Recherche Agronomique (INRA) in France, 'Mesembrine' has been asexually propagated by grafting in France and in Parker, Wash., USA, and has been observed to remain true to type over successive asexually propagated generations.

'Mesembrine' was selected for its broad oblate shape and pleasant sub-acid flavor. While similar in many respects to 'S 6816' (plant patent pending), the fruit of 'Mesembrine' matures one to two weeks later. It has also been observed that the leaves of 'Mesembrine' are longer than those of 'S 6816.'

DETAILED BOTANICAL DESCRIPTION OF THE VARIETY

The following detailed botanical description is based on observations of four year old trees made during the 2004 growing season at Parker, Wash. The test trees were grown on 'Lovell' (unpatented) rootstock. All colors are described according to The Royal Horticultural Society Colour Chart.

It should be understood that the characteristics described will vary somewhat depending upon cultural practices and climatic conditions and can vary with location and season. Quantified measurements are expressed as an average of measurements taken from a number of individual plants of the new variety. The measurements of any individual plant, or any group of plants, of the new variety may vary from the stated average.

Tree:
- *Type.*—Non-spur type.
- *Vigor.*—Medium.
- *Habit.*—Upright.
- *Size.*—Width 2.2 m; height 3.9 m.
- *Production.*—Heavy.

Trunk:
- *Size.*—Diameter 34.1 at base.
- *Bark.*—Texture varies; color grey 201D on very rough bark; greyed-purple 183A on rough bark; greyed-purple 184A on smooth bark.
- *Lenticels.*—Large, prominent, length 0.8 to 1.1 cm; 10 per square inch; color orange-white 159A.

Flowering branch:
- *Size.*—Length 50.8 cm; diameter 1.6 cm.
- *Texture.*—Smooth.
- *Length of internodes.*—Medium, 2.2 to 2.5 cm.
- *Color.*—Greyed-purple 184A.
- *Anthocyanin coloration.*—Present.
- *Intensity of anthocyanin coloration.*—Medium.

Flowers:
- *Abundance of flower buds.*—Medium.
- *Distribution of flower buds.*—Generally in groups of two or more.
- *Time of beginning of flowering.*—Bud burst March 18; bloom period March 21 to Apr. 6, 2005.

*Buds.*—Length 0.8 to 0.9 cm; elongated with rounded tip; color red-purple 59A, tip red-purple 63B; hardy.
*Flower shape.*—Rosaceous.
*Fragrance.*—Fragrant, not sweet.
*Flower size.*—Diameter 3.6 to 3.9 cm.
*Calyx color* (*open flower before falling of petals*).—Orange.
*Petals.*—Quantity 5; overlapping; large, length 1.5 to 1.6 cm, width 1.4 to 1.5 cm; margins ruffled; petal texture smooth; color upper surface red-purple 62D, lower surface red-purple 61D.
*Number of pistils.*—Always one.
*Position of stigma compared to anthers.*—Below.
*Stamen length compared to petals.*—Shorter.
*Anthers.*—Size 0.05 cm; color greyed-red 180A; pollen present, yellow 1A.
*Pubescence of ovary.*—Absent.
*Stamen.*—Quantity 36; length 1.0 to 1.2 cm; color red-purple 62D.
*Filament.*—Size 0.9 to 1.1 cm.
*Pistil.*—Size 1.0 to 1.2 cm; color yellow 1A.
*Sepals.*—Length 0.5 to 0.6 cm; width 0.3 to 0.4; color red-purple 59A.
*Fertility.*—Self-fertile.

Leaves:
*Time of leaf bud burst.*—Medium.
*Size.*—Medium, length 13.0 cm, width 4.0 cm.
*Ratio length/width.*—Medium.
*Profile.*—Flat.
*Curvature of tip.*—Recurved downward.
*Angle at base.*—Nearly right angle.
*Angle at top.*—Medium.
*Anthocyanin coloration.*—Absent.
*Color.*—Yellow-green 146A with yellow-green 146D spots.

Petiole:
*Length.*—Medium, 1.5 cm.
*Nectaries.*—Present.
*Shape of nectaries.*—Kidney-shaped.
*Number of nectaries.*—Normally two.

Fruit:
*Size.*—Small, diameter 7.0 cm; height 4.0 cm.
*Shape in profile view.*—Broad oblate.
*Shape of tip.*—Bowl shaped depressed.
*Symmetry when cut along suture.*—Symmetric.
*Suture.*—Marked.
*Depth of petiole cavity.*—1.5 cm.
*Width of petiole cavity.*—2.5 cm.
*Color of skin.*—Ground color orange-red 34B; over color red-purple 59A.
*Extension of anthocyanin coloration of skin.*—Very large.
*Pubescence.*—Absent.
*Lenticels.*—Absent.
*Thickness of skin.*—Medium.
*Adherence of skin.*—Medium.
*Firmness of flesh.*—Very firm.
*Anthocyanin coloration directly under skin.*—Absent.
*Anthocyanin coloration around the stone.*—Present.
*Texture of the flesh.*—Not fibrous, fine, melting.
*Sugar content of flesh.*—High, Brix 13.5.
*Color of flesh.*—Yellow 16C; color near seed yellow N30A.
*Flavor.*—Sub-acid, skin slightly tart.

Stone:
*Size compared to fruit.*—Small, diameter 2.5 cm.
*Shape.*—Flat; ridged; pitted.
*Color.*—Red-purple 59B.
*Likelihood of stone to split.*—Absent or very weak.
*Adherence to flesh.*—Yes.
*Degree of adherence to flesh.*—Medium.

Maturity:
*Bearing.*—Annual.
*Time of maturity.*—Early (Aug. 4, 2004 at Parker, Wash.).
*Duration.*—Multiple pickings.
*Preharvest drop.*—Absent or minimal.
*Time of falling of leaves.*—Medium.
*Resistance to pests and diseases.*—None noted.

We claim:

1. A new and distinct nectarine tree, named Mesemabrine, substantially as shown and described herein.

* * * * *